US008645171B2

(12) United States Patent
Lutgen et al.

(10) Patent No.: US 8,645,171 B2
(45) Date of Patent: *Feb. 4, 2014

(54) SYSTEM AND METHOD OF DRUG DISEASE MATCHING

(75) Inventors: Gerald Lutgen, St. Paul, MN (US); Tomas Valdivia, Inver Grove Heights, MN (US); Krista Van Vorst, Minneapolis, MN (US); Adam Bock, Bloomington, MN (US)

(73) Assignee: OptumInsight, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/612,164

(22) Filed: Sep. 12, 2012

(65) Prior Publication Data

US 2013/0030842 A1 Jan. 31, 2013

Related U.S. Application Data

(63) Continuation of application No. 09/571,648, filed on May 15, 2000, now Pat. No. 8,301,468.

(51) Int. Cl.
*G06Q 40/00* (2012.01)
(52) U.S. Cl.
USPC .................................................. 705/4
(58) Field of Classification Search
USPC .................... 705/2–4; 600/300–301
See application file for complete search history.

(56) References Cited

U.S. PATENT DOCUMENTS

| 5,018,067 | A | * | 5/1991 | Mohlenbrock et al. | ....... | 600/300 |
| 5,099,424 | A | * | 3/1992 | Schneiderman | ................... | 705/3 |
| 5,404,292 | A | * | 4/1995 | Hendrickson | ................. | 600/301 |
| 5,486,999 | A | * | 1/1996 | Mebane | ............................ | 705/2 |
| 5,544,044 | A | | 8/1996 | Leatherman | | |
| 5,557,514 | A | * | 9/1996 | Seare et al. | ....................... | 705/2 |
| 5,594,638 | A | * | 1/1997 | Iliff | .................................. | 705/3 |
| 5,715,451 | A | * | 2/1998 | Marlin | ................................. | 1/1 |
| 5,835,897 | A | | 11/1998 | Dang | | |

(Continued)

FOREIGN PATENT DOCUMENTS

WO      WO 99/44167      9/1999

OTHER PUBLICATIONS

Ingenix Announces New Clinical Care Groups' Episode Grouping Tool with Integrated Pharmaceutical Data, Apr. 11, 2000. Ingenix, Inc. [Retrieved from the Internet on Oct. 21, 2002]. URL: <http://www.ingenix.com/releases/4-11-00.html>.
Ingenix Products and Services. May 11, 2000. Ingenix, Inc. [Retrieved from the Internet on Aug. 20, 2003]. URL: <http://web.archive.org/web/20000511154002/www.ingenix.com/products/products.html>.

(Continued)

*Primary Examiner* — Lena Najarian
*Assistant Examiner* — Natalie A Pass
(74) *Attorney, Agent, or Firm* — Bridget M. Hayden; Dorsey & Whitney LLP

(57) ABSTRACT

A computer implemented system and method for matching drugs and diseases involves matching drugs identified in a specific patient's prescription claim records with diseases identified in the patient's medical claims. A weighted relationship is generated between the matched drugs and diseases by calculating a link weight in accordance with a preprogrammed formula for each of the diagnosis codes identified in the patient's medical claims that is identified as associated with the disease identified and the drug. The link weight provides a statistical match association value to each of the matched diseases identified by way of a diagnosis code in the patient's medical claim and the drug identified in the prescription claim.

13 Claims, 13 Drawing Sheets

(56) References Cited

U.S. PATENT DOCUMENTS

| | | | |
|---|---|---|---|
| 5,956,689 A | | 9/1999 | Everhart, III |
| 5,970,463 A | * | 10/1999 | Cave et al. .................. 705/3 |
| 5,976,082 A | * | 11/1999 | Wong et al. ................ 600/300 |
| 6,000,828 A | | 12/1999 | Leet |
| 6,112,182 A | * | 8/2000 | Akers et al. .................. 705/2 |
| 6,370,511 B1 | * | 4/2002 | Dang .......................... 705/3 |
| 6,587,829 B1 | | 7/2003 | Camarda et al. |
| 6,687,685 B1 | * | 2/2004 | Sadeghi et al. ............. 706/15 |
| 7,124,031 B1 | * | 10/2006 | Hoffman et al. ............ 702/19 |

OTHER PUBLICATIONS

A New World of Health Intelligence. Ingenix Web Site, Mar. 2, 2000. [Retrieved on Nov. 3, 2002]. Retrieved from the Internet: <URL: http://web.archive.org/web/20000311023529/www.ingenix.com/main.html>.

Imagine if You Could Obtain Accurate Clinical Data from the Point of Care. MD Trends Web Site. Dec. 4, 2000. [Retrieved on Nov. 3, 2002]. Retrieved from the Internet: <URL: http://web.archive.org/web/20001204191600/www.mdtrends.com/>.

* cited by examiner

SYSTEM AND METHOD OF DRUG DISEASE MATCHING

This application is a continuation of U.S. patent application Ser. No. 09/571,648, filed May 15, 2000, entitled "System and Method of Drug Disease Matching," issued as U.S. Pat. No. 8,301,468 on Oct. 30, 2012, the content of which is hereby incorporated in its entirety by reference.

TECHNICAL FIELD

The present invention relates generally to a computer implemented system and method of processing and analyzing medical and prescription claims information. More particularly, the present invention relates to a computer-implemented system and method for analyzing prescription and medical claims data relating to a patient's medical history, and processing the prescription and medical claims history data to generate a statistical relationship between drugs and diseases.

BACKGROUND OF THE INVENTION

The use of administrative claims data for reporting of healthcare costs and utilization is a relatively new phenomenon in the 1990's. Cost pressures due to increasing medical costs have caused health plans and insurers to look for new ways to understand what the health care dollar is buying. Furthermore, demands from employer groups and other healthcare payers have spawned a "quality of care" movement that has incentivised health plans to publicly report various aspects of their care delivery (e.g., by producing HEDIS reports) and to seek accreditation from the National Committee for Quality Accreditation or other accrediting body. Claims data, or electronic records of services and products paid for by a health plan for its insured population, have been instrumental in providing the information needed for cost, utilization, and quality reporting.

Much of health plan reporting focuses on particular illnesses or procedures and thus utilizes mainly medical claims submitted by physicians and facilities such as hospitals. Pharmacy claims, however, remain a largely untapped resource for analysis. Pharmacy claims have been used in certain quality of care analyses, such as identifying beta blocker usage for patients who have had heart attacks. Pharmacy claims have also been used to identify patients with particular diseases, such as diabetes. However, pharmacy claims data have not been used in a broad way to supplement—or even replace—analyses using medical claims data. The main reason for this is the fact that pharmacy claims do not contain diagnosis codes or any other information that would indicate why the drug was prescribed for a particular patient. Thus using pharmacy claims in various types of analysis requires one or more clinicians to manually determine, for each drug, all the diseases the drug is used to treat. This process is not feasible due to the time and resource constraints for most analytic needs.

Given these resource constraints, there is a need for a comprehensive, organized system that identifies the disease related uses for all drugs. Optimally, this system would be easy for health plans, large employers, or any other company with large claims databases to implement and maintain. The optimal system also would be updated periodically to provide information on the newest drugs approved by the FDA. The present invention was designed with these goals in mind.

SUMMARY OF THE INVENTION

The present invention is a computer implemented system and method for matching drugs and diseases and generating a weighted relationship between the matched drugs and diseases. The computer implemented system includes at least a first memory area for storing a quantity of patient medical history billing records identifiable as patient prescription claim records and medical claim records, including provider and facility medical claims. The system further includes a second memory area for storing a grouping of drug codes and groupings of diagnosis codes and a processor coupled to the first and second memory areas. The computer implemented system includes a drug disease matching module that configures the processor to match drugs identified in a specific patient's prescription claim records with the diagnosis codes on medical claims within the patient medical history by performing the following steps: identifying at least one prescription claim for a specific patient from the patient's prescription claim records; identifying at least one drug by its drug identification code for the identified at least one prescription claim; identifying at least one disease associated with the identified at least one drug; and identifying patient medical claims for the specific patient associated with the at least one disease identified, wherein each patient medical claim identified may have at least one diagnosis code associated with said at least one disease identified. The system generates a weighted relationship between the matched drugs and diseases by calculating a link weight for each claims data occurrence of the diagnosis codes associated with the at least one disease and the drug in accordance with a preprogrammed algorithm. The link weight provides a measure of association between drug identified and each disease by way of a diagnosis code within each of the patient medical claims identified as associated with the disease identified. For drug claims that are linked to more than one indicated disease, the program summarizes the link weight information and ranks diseases in order of increasing likelihood that the drug was prescribed for that disease.

These and various other features as well as advantages, which characterize the present invention, will be apparent from a reading of the following detailed description and a review of the associated drawings.

DETAILED DESCRIPTION OF THE INVENTION

Figure 1:
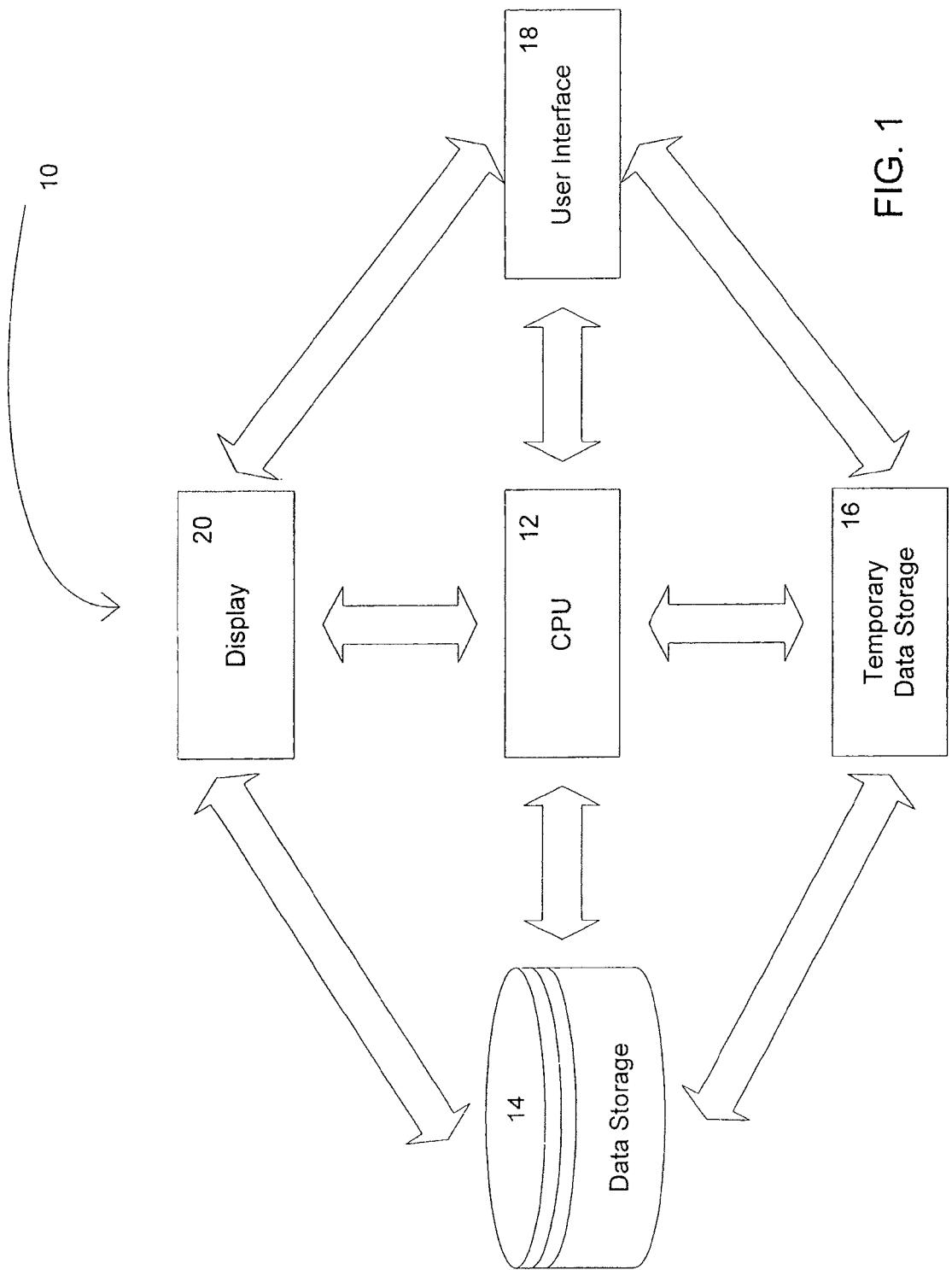
FIG. 1 illustrates the hardware structure of the present computerized system.

In the following detailed description of the preferred embodiment, reference is made to the accompanying drawings that form a part hereof and in which is shown by way of illustration a specific embodiment in which the invention may be practiced. This embodiment is described in sufficient detail to enable those skilled in the art to practice the invention and it is to be understood that the other embodiments may be utilized and that structural or logical changes may be made without departing from the scope of the present invention. The following detailed description is, therefore, not to be taken in a limiting sense, and the scope of the present invention is defined by the appended claims.

Overview

The present invention comprises a computer implemented system for and method of processing prescription and medical claims to generate a relationship between drugs and diseases. It is envisioned that health plans, large employer groups, and other payers of prescription and medical claims who have administrative data for a large population of insured persons (i.e., Medicaid programs for a given state) will utilize the drug disease matching module of the present invention to analyze patterns of drug treatment for the population. Using the output of the present invention, a data analyst can perform such functions as identifying the diseases for which patients are being prescribed various drugs; identifying drugs that have been prescribed to patients that do not have matching disease indications in their medical claims data; and determining the number of days between an office visit or physician patient encounter and a prescription. Functions that generate information of this type can be used to identify and support quality improvement and research activities. For example, a health plan may be concerned that patients receiving certain medications are not following up with their physicians as often as they should. If analysis revealed that most prescriptions for anti-hypertensive medication occurred more than 180 days after an office visit for hypertension, the health plan may issue a recommendation that patients receiving these drugs see their physicians at least twice a year. The same analysis could be done for drugs for other chronic conditions, such as anticoagulants, antipsychotics, and antiepileptics. Furthermore, a high proportion of pharmacy claims with no medical claim matches might suggest that patients are not seeing their physicians enough, that physicians are not coding the appropriate diagnoses to match the drugs they prescribe, or that physicians are prescribing drugs without accompanying office visits, for example, as a result of a phone call with the patient. The present invention generates data that will assist with pinpointing these potential problem areas for further analysis and possible quality improvement programs.

The present invention can also be used to examine costs of pharmaceutical usage in a population of insured persons. An analysis of drug cost may also inform potential quality improvement programs and areas for further research. For example, if a large proportion of the total cost paid for a particular drug is linked to a disease that is an indicated, but unlabeled use for that drug, health plan clinicians might investigate whether or not a better, more cost-effective drug or alternative therapy exists for that condition.

When combined with output from other software tools that group medical claims into episodes of care, the present invention's output can be used to bring the cost of pharmacotherapy into the various disease category costs. For many conditions, the total cost of care is highly driven by pharmaceutical usage; thus the present invention adds a critical component to the overall healthcare cost picture.

Administrative claims data from a large insured population can be processed using the present invention and its output analyzed to determine the most frequent uses for various drugs. This information in turn can serve as "benchmark" data that can be generalized to other populations. For example, a pharmaceutical or other type of health care company might have drug data but no medical claims to which to link drugs to diseases for that population. The benchmark data could be used to impute the diseases that the drugs were likely prescribed to treat for the population, in essence, filling in for the missing medical claims data. In cases where both pharmacy and medical claims are available for a population, benchmark data can be used to compare drug treatment patterns in different populations. Comparisons of drug prescribing for various conditions across different geographic regions, in different practice settings, or across time would also be possible using this drug use benchmark data. For example, a small health plan could compare its resultant data generated by the present invention to those of a national benchmark database to determine if drug treatment patterns are reasonably similar. Cases where drug treatment patterns were dissimilar might require the health plan to investigate why a particular drug is or is not being prescribed.

Analysts in academic or governmental settings may also find DDM output useful. Health services research is a largely academic field focused on the study of health care management, delivery, and outcomes. Research is usually funded in the form of grants to individual principal investigators to do one or more discrete studies. The present invention is an easy-to-use tool to quickly access drug-disease information on a population; without a system and method of processing data like the present invention, investigators must identify and write programs for every condition or treatment they wish to study, which is both costly and time-consuming. In a study of diabetes, for example, output resulting from processing of drug and disease data by the present invention could be used to determine the comorbidities that diabetic patients in the study population have, based on all their pharmaceutical usage and the diseases the program has linked the drugs to.

Software products that group medical claims data into episodes may not bring in pharmaceutical claims data, or may do an inadequate job of incorporating drug data into the episodes. The drug disease matching module that implements an embodiment of the present invention could be used in conjunction with an episode grouper in order to accurately assign pharmacy claims to specific episodes of care. An episode grouper is a software product module that groups medical claims into episodes. An example of an episode grouper is disclosed in U.S. patent application Ser. No. 08/539,413, which is assigned to Ingenix Inc., is incorporated herein by reference as if fully set forth herein. Another episode grouper module, owned and developed by Ingenix which may be used and is discussed below, is the Clinical Care Group ("CCG").

General Description of Invention

The present invention is a computer implemented system and method for processing a plurality of pharmacy and medical claims one patient at a time in order to generate a relationship between drugs and diseases. The computer implemented system performs a method of processing a plurality of pharmacy and medical claim records for a plurality of patients one patient at a time by performing the following steps. First, a pharmacy claim for a specific patient is identified. The drug for which the prescription is written is identified and its drug indication number is extracted. Next, the indicated disease(s) and associated ICD-9 diagnosis codes for the drug identified in the pharmacy claim are determined. Next, the patient's medical claims stream is searched for instances of any and all diagnosis codes that match the ICD-9 diagnosis codes for the indicated disease. The search is forward and backward and thereby includes instances in a patient's history that may have occurred before and after the pharmacy claim. When instances of the diagnosis code for the indicated disease are found, the strength of the relationship between the located diagnosis code and the pharmacy claim is determined by assessing several characteristics of the pharmacy and medical claims that constitute each match. For pharmacy claims that are matched to medical claims having more than one indicated disease, the diseases are ranked in order of strength of match to the pharmacy claim. Next, a report may be generated summarizing the matching information for each pharmacy claim. In another embodiment, the system may also classify the drugs identified from the pharmacy claims processed into drug categories that are large enough to produce a manageable number of classes, and summarize the disease matching information for each drug class. The summarized drug classes in the alternative embodiment that have multiple indicated diseases resulting from a query of medical claims ranks the diseases in order of importance. Finally, the system creates output files having summary information for the respective data generated.

FIG. 1 is a diagram illustrating the computer hardware system 10 for implementing the software processing of the present invention. The computer system 10 may be implemented with a wide variety of computers, such as desktop or laptop computers. Connected to a common computer bus, are several operating units that form the computer system. These are a central processing unit (CPU) 12, data storage 14, temporary data storage 16, user interface 18, and a display device 20. The data storage device 14, is the part of the system shown in FIG. 1 that contains the information comprising patient medical history, which includes, patient medical claims and patient pharmacy claims. Data storage 14 also includes a plurality of lookup tables, that link the National Drug Codes (NDC) on pharmacy claims to disease diagnosis codes (ICD-9 diagnosis codes) on medical facility and provider claims. The NDC code serves as a standard, universal product identification number for drugs used to treat humans. ICD-9 diagnosis codes are an international classification standard for diseases that are routinely used by facilities and providers when submitting claims to health plans for payment for services provided to health plan members. More specifically, the lookup tables include a Service and Facility Category Code table, an NDC-DIN table, a DIN-ICD table, Master Drug-to-Diagnosis Code table, DIN-CCG table and a CCG-ICD-9 table. The Service and Facility Category Code table provides a list of procedure codes that must appear on a medical claim for the claim to be eligible to be linked to a pharmacy claim. The fields included in the Service and Facility Category Code table include at least the following: Service Category ID and CPT/HCPC code, or Revenue code. The Service Categories for eligible claims are set forth in Table #1 below

TABLE 1

| Category | Description |
|----------|-------------|
| EA | Ambulatory evaluation and management |
| EI | Inpatient evaluation and management |
| ER | Outpatient emergency |
| EU | Unknown/other evaluation and management |
| MD | Diagnostic medicine |
| MT | Therapeutic medicine |
| MU | Unknown/other medicine |
| PSU | Professional services unknown/other |
| RT | Radiation therapy |
| SD | Diagnostic surgery |
| ST | Therapeutic surgery |
| SU | Unknown/other surgery |
| W | Preventative |

The Service Category for claims that are ineligible to be linked to pharmacy claims are set forth below in Table 2.

TABLE 2

| Category | Description |
|----------|-------------|
| A | Anesthesia |
| AC | Access |
| AD | Administrative |
| G | Supplies |
| GT | Supplies - transport |
| ISD | Imaging - Diagnostic surgery |
| IST | Imaging - Therapeutic surgery |
| ISU | Imaging - Unknown/other surgery |
| J | General adjunct |
| L | Laboratory |
| P | Pathology |
| RD | Diagnostic radiology |
| RX | Pharmacy |
| T | Transport |

The Facility Category Codes for eligible claims are set forth in Table 3 below.

TABLE 3

| Category | Description |
|----------|-------------|
| AMS | Ambulatory surgery |
| CAR | Cardiology |
| CLI | Clinic |
| EMR | Emergency room |
| GIS | Gastrointestinal services |
| HPC | Hospice |
| INC | Nursing |
| IRD | Inpatient renal dialysis |
| LIT | Lithotripsy |
| LRD | Labor and delivery |
| MSD | Miscellaneous dialysis |
| MSS | Medical social services |
| OHD | Outpatient hemodialysis |
| ONC | Oncology |
| OPT | Outpatient services |
| ORS | Operating room services |
| OST | Osteopathic services |
| OTR | Occupational therapy |
| OTC | Other training services |
| PCS | Vaccine administration |
| PRO | Professional services |
| PSY | Psychiatric services |
| PTD | Peritoneal dialysis |
| PTR | Physical therapy |
| RBD | Room and board |
| REC | Recovery room |
| RES | Respiratory services |
| SKN | Skilled nursing |
| SLP | Speech therapy |
| THR | Therapeutic radiology |
| TOR | Treatment or observation room |

The Facility Category Codes for claims that are ineligible to be linked to pharmacy claims are set forth below in Table 4.

TABLE 4

| Category | Description |
| --- | --- |
| BHP | Board hospice, general, other inpatient |
| GHH | Oxygen home health |
| GR | Casting services |
| HH | Home health |
| MTH | Home IV therapy |
| RU | Radiology unknown, nuclear medicine |
| RXT | Ambulance, pharmacy |

The NDC-DIN lookup table establishes a link between the NDC code on a prescription claim and a Drug Identification Number (DIN). It contains one observation per NDC code, with the following fields: NDC and Drug Identification Number.

The DIN-ICD lookup table establishes a link between DINs and ICD-9 diagnosis codes listed in a standard state of the art, "unexpanded," or "original" drug-disease indications file. This state of the art file is commercially available from a national vendor of electronic pharmaceutical data. This file contains one observation per DIN-ICD-9 code and is important because higher weight is given to ICD-9 codes that are on this list than those that appear on the expanded list. The fields contained in the DIN-ICD lookup table include Drug Indication Number and ICD-9 code.

The expanded DIN-CCG table was developed to overcome the shortcomings of the state of the art drug-disease file. The fields contained in the expanded DIN-CCG table include the following: Drug Indication Number and CCG Class number. The CCG-ICD-9 table provides a list of ICD-9 codes that define each CCG Class. The fields contained on this file include: Clinical Care Groups disease class, and ICD-9 diagnosis code.

The DIN-CCG and CCG-ICD-9 tables are merged to create the Master Drug-To-Diagnosis Code lookup table that is representative of an expanded ICD-9 diagnosis code table of links between DINs and ICD-9 diagnosis codes.

The standard state of the art "unexpanded" drug-disease files are inadequate for use in the present invention for several reasons. First, the file contains ICD-9 diagnosis codes that represent the most general, or non-specific, form of the disease. For example, for the entry "Mental depression," the file lists a single ICD-9 code, 311, which is "Depressive disorder, not elsewhere classified." There are several ICD-9 codes for more specific types of depression that are omitted from this list, for example, 296.2 and 296.3, for "Major depressive disorder, single episode" and "Major depressive disorder, recurrent episode," respectively. Second, the state of the art files contain several thousand disease indications, which results in an unwieldy number of disease categories to work with. For example, these files contain entries for "Akinetic epilepsy," "Tonic-clonic epilepsy," "Jacksonian epilepsy," and other variants of epilepsy; what is desired for the present invention, however, is a broader disease category of "Epilepsy."

To overcome the shortcomings of the narrowly defined ICD-9 lookup table, broader disease definitions from the Clinical Care Groups software module were used. New lookup tables were developed using the ICD-9 code that define each disease.

In building the specific CCG ICD-9 drug-disease lookup tables, the following steps were taken. First, the disease indications from the state of the art file were examined and where appropriate, a small number of ICD-9 codes for more specific instances of a disease were added to the non-specific code in the database. For example, for the disease "Diptheria," the narrowly defined ICD-9 lookup table included only ICD-9 code 032.9, which stands for "Diptheria, Unspecified." The category for the disease "Diptheria," was broadened by including in the list of ICD-9 codes for diptheria additional codes such as, for example, 032.0 (Nasopharyngeal diptheria), 032.1 (Anterior nasal diptheria), 032.3 (Laryngeal diptheria), and all codes beginning with 032.8 (Other specified diptheria). After the list of ICD-9 codes for specific diseases were broadened, the ICD-9 codes were mapped to CCG classes and each disease was broadened to contain all ICD-9 codes within that CCG class. Thus the list of ICD-9 codes for each disease consists of (a) the ICD-9 codes from the original drug-disease files, (b) any specific ICD-9 codes added to the nonspecific codes, and (c) any other ICD-9 codes contained in the disease class or classes that the codes from (a) and (b) map to. A detailed example of this mapping is shown below in Tables 4, 5 and 6. Finally, the disease indications for all drugs were reviewed and CCG classes were added, where appropriate. The CCG disease classification system from which the ICD-9 codes were mapped is derived from the CCG disease classification system set forth in U.S. patent application Ser. No. 08/539,413. Expanding the indicated diseases into broader disease categories allows a wider range of ICD-9 codes to produce links between a particular drug and medical claims diagnoses, and it also produces a more manageable number of diseases for purposes of reporting and analysis.

While it is the intent of the present invention to have as many drugs as possible linked to specific disease categories, some drugs link to non-specific disease categories, which are not suitable for creating an expanded ICD-9 code list. Examples of such non-specific disease categories are listed below in Table 5:

TABLE 5

| Class | Description |
| --- | --- |
| 21X | Other benign or Unsp neoplasm |
| 940 | Other Burns |
| 745X | Other cardiovascular congenital abnormalities |
| 39X | Other cardiovascular disorders |

In order to explain in greater detail the creation of the Master Drug-to-Diagnosis Code lookup table, the following example describes such creation using a specific drug, Atenolol, a beta-blocker. The original state of the art drug-disease file lists the following indicated diseases:

TABLE 6

Original Drug-Disease File Listing of Indicated Diseases for Atenolol

| Disease/Condition | ICD-9 Code | ICD-9 Code Description |
| --- | --- | --- |
| Thyrotoxicosis | 242.90 | Thyrotoxicosis NOS* |
| Hypertension | 401.9 | Hypertension NOS |
| Myocardial reinfarction prophylaxis | 410.90 | Acute Myocardial Infarction NOS |
| Angina pectoris | 413.9 | Angina Pectoris NEC**/NOS |
| Mitral valve prolapse | 424.0 | Mitral Valve Disorder |

TABLE 6-continued

Original Drug-Disease File Listing
of Indicated Diseases for Atenolol

| Disease/Condition | ICD-9 Code | ICD-9 Code Description |
|---|---|---|
| Hypertrophic cardiomyopathy | 425.4 | Primary Cardiomyopathy NEC |
| Arrhythmias, cardiac | 427.9 | Cardiac Dysrhythmia NOS |
| Tremors | 781.0 | Abnormal Involuntary Movement |
| Vascular headache | 784.0 | Headache |

*Not otherwise specified
**Not elsewhere classified

As Table 6 illustrates, Atenolol contains many ICD-9 codes that are for "nonspecific" or "not elsewhere classified" manifestations of the indicated diseases, and where necessary, the physician consultant added more specific ICD-9 codes. In this example, the physician consultant added one code to the original code for angina pectoris, 413.0 ("Angina decubitus"). Next, the list of ICD-9 codes—the original and physician-added list—are then mapped to a file containing all ICD-9 codes that define each CCG disease category. Table 7 illustrates the CCG classes for Atenolol that are mapped from the list of original and physician added ICD-9 codes.

TABLE 7

| CCG Class | Description |
|---|---|
| 242XX | Hyperthyroidism, Except in Pregnancy |
| 39X | Other Cardiovascular Disorders |
| 396X | Valvular Heart Disease |
| 40X | Essential Hypertension With End-organ Complication |
| 401 | Essential Hypertension Without End-organ Complication |
| 410XX | Acute Myocardial Infarction |
| 4140 | Ischemic Heart Disease |
| 4257 | Nonalcoholic Cardiomyopathy |
| 7800X | Symptoms, Signs and Ill-defined Conditions |
| 7840 | Headache |

All ICD-9 codes in most of the CCG classes are brought into the drug-disease lookup table as indications for the drug Atenolol. There are two non-specific CCG classes in Table 7 that have ICD-9 codes that are not incorporated into this file. Those non-specific CCG classes are 39×, "Other Cardiovascular Disorders" and 7800×, "Symptoms, Signs, and Ill-Defined Conditions." Only one code from each of these classes will be used, 427.9 and 781.0, respectively (as shown above in Table 6).

The final list of CCG classes for Atenolol is shown in Table 8. All ICD-9 codes for these classes (with the two exceptions mentioned above) are added to the drug-disease lookup table as indicated diseases for Atenolol. Finally, physician consultants review the list of disease categories and determine if there are missing diseases. Where appropriate, they add diseases to the list of indications for each drug. For example, the consultant added several diseases for Atenolol, including migraine, unstable angina, and secondary hypertension.

TABLE 8

Final List of Indicated Disease Classes for Atenolol

| CCG Class | Description |
|---|---|
| 242XX | Hyperthyroidism, Except in Pregnancy |
| 3000X | Anxiety and Neurotic Disorders Except Minor Depression |
| 346XX | Migraine |

TABLE 8-continued

Final List of Indicated Disease Classes for Atenolol

| CCG Class | Description |
|---|---|
| 39X | Other Cardiovascular Disorders |
| 396X | Valvular Heart Disease |
| 40X | Essential Hypertension With End-organ Complication |
| 401 | Essential Hypertension Without End-organ Complication |
| 405XX | Secondary Hypertension |
| 410XX | Acute Myocardial Infarction |
| 4111 | Unstable Angina |
| 4140 | Ischemic Heart Disease |
| 4255 | Alcoholic Cardiomyopathy |
| 4257 | Nonalcoholic Cardiomyopathy |
| 427 | Paroxysmal Supraventricular Tachycardia |
| 4271 | Paroxysmal Ventricular Tachycardia |
| 4273X | Atrial Fibrillation and Flutter |
| 4276X | Premature Beats |
| 428X | Heart Failure |
| 7800X | Symptoms, Signs and Ill-defined Conditions |
| 7840 | Headache |

Pharmacy claims, provider claims and facility claims for patients are stored in system data storage as individual records. A record consists of a single service or billing line item. In using pharmacy claims, provider claims and facility claims for reporting of healthcare costs and utilization, there may be multiple records for what would be commonly considered to be a "visit" or "encounter." Accordingly, the terms "record," "claim line," and "claim" are used interchangeably and refer to a line item of data relating to the provision of health care services or products. The term "visit" refers to the entirety of claim records associated with a face-to-face encounter between a provider and a patient on a given date of service.

In processing a plurality of pharmacy and medical claim records, the present invention sorts the records by patient and ascending date of service order. The fields shown in Table 9 below illustrate the fields necessary for processing of provider and facility claim records.

TABLE 9

Audit number (unique service identification number)
Member ID
ICD-9 diagnosis codes (up to 6 diagnoses)
Date of service
CPT-4 procedure code, or revenue code The fields shown in Table 10 below illustrate the fields necessary for processing of pharmacy claim records.

TABLE 10

RX claim number (unique RX claim ID number)
Member ID
NDC code
Date of service (fill date)

In one embodiment, the present invention uses the provider ID number and provider specialty in assigning diseases to drugs. In another embodiment, the present invention processes pharmacy and medical claim records without the use of data representative of provider ID number and provider specialty.

As mentioned above, the present invention processes pharmacy, provider, and facility claims one patient at a time. For each patient with both pharmacy and medical claims, the program separates the claims into the two claim types, pharmacy and medical. The present embodiment of the invention processes pharmacy records first. After a pharmacy record is identified, three lookup tables stored in system data storage are accessed. The first lookup table maps the identified pharmacy claim's NDC code to a drug ID number (DIN). This drug ID number essentially groups NDC codes that correspond to the same drug (for example, the DIN 00245 groups all NDC codes corresponding to Atenolol 100 mg, 50 mg, and 25 mg tablets). The second lookup table is accessed by drug ID number and provides the ICD-9 diagnosis codes listed on the original disease indications file. The third table is also accessed by drug ID number and provides the expanded list of ICD-9 codes for all indicated diseases for each DIN. The drug ID number and the list of indicated ICD-9 codes are stored in a temporary file.

Next, the patient's medical claims history is searched for eligible medical claims having ICD-9 diagnosis codes that match the ICD-9 codes identified and stored in the temporary file. There are several parameters that define how the program searches for matching medical claims. In one embodiment, a first parameter is the search for matches in a patient's medical claims history within a specific time frame. For example, the date of service on the medical claim must be up to 365 days before and 31 days after the fill date of the prescription. This time frame allows for matches between drugs used to treat chronic conditions and office visits occurring in the past. For some patients with chronic conditions, office visits may be infrequent but the patient may receive several months' worth of refills at each visit. The present embodiment of the invention also provides for the generation of drug-specific time frames within which to search for medical claims. Such time frames, for example, might be determined based on some measure of chronicity of each disease indicated for the drug. A second parameter is the searching for matching ICD-9 codes in primary and all secondary diagnosis fields on the medical claims. A third parameter is the matching of pharmacy records only to-medical claim records that are indicative of face-to-face encounters with providers. Medical claims that are for face-to-face visits, are within the specified time frame, and contain ICD-9 codes on the list of indicated diseases for that drug constitute links with the pharmacy claim. In most cases, a link is a match between a pharmacy claim and a medical claim; however, if a single medical claim contains two or more ICD-9 codes that are on the list of indicated diseases, each ICD-9 code on that claim will constitute a separate link. Therefore, a single medical claim can generate multiple links with a given pharmacy claim.

A link is a pair of claims, one pharmacy and one physician or facility, that constitute a drug-disease match. A match is formed when the ICD-9 diagnosis code on the physician or facility claim is a disease for which the drug on the pharmacy claim is indicated in one embodiment, and the pharmacy claim fill date occurs within a pre-specified number of days before or after the date of service on the medical claim. It is to be understood that it is contemplated that in other embodiments, there may be no day(s) limit on the number of days before or after the date of service on the medical claim.

After a link has been established between a pharmacy and a physician or facility claim, the present embodiment of the invention calculates a score, or weight value, that represents the degree of confidence that the prescribed drug was actually prescribed for the diagnosis the present embodiment of the invention identified. This value is called the link weight. In the current embodiment of the invention, five characteristics of the pharmacy and medical claims that constitute the link are assessed when the link weight is calculated. For each pharmacy-medical claim link, the program assesses each of the five characteristics, assigns a numeric value to each, and then adds together these five values to arrive at the link weight value. These five characteristics are:

The number of days between the date of service on the medical claim and the fill date of the prescription;
   Whether the physician submitting the medical claim was the same as the prescribing physician on the pharmacy claim;
   Whether the diagnosis code on the medical claim was listed as the primary diagnosis;
   Whether the diagnosis code is listed in the original, "unexpanded" drug-to-disease file;
   Whether the physician submitting the medical claim belongs to the same specialty as the prescribing physician.

The present invention contains a lookup table that provides numeric values associated with each characteristic. The values in the lookup table provide an assessment of the importance of each criterion relative to the others; higher values indicate greater importance. This lookup table is depicted in Table 11 below.

TABLE 11

| Components of Link Weight Value | | |
|---|---|---|
| 1. | Number of days between medical and pharmacy claim* | |
| | Same day - pharmacy claim 1 day after medical | Time Weight A |
| | 1 day before, 2-3 days after | Time Weight B |
| | 2-3 days before | Time Weight C |
| | 4-7 days before, 4-7 days after | Time Weight D |
| | 8-14 days after | Time Weight E |
| | 15-31 days after | Time Weight F |
| | 8-14 days before, 32-93 days after | Time Weight G |
| | 14-31 days before, 94-124 days after | Time Weight H |
| | 125-365 days after | Time Weight I |
| | More than 31 days before; More than 365 days after | 0 |
| 2. | Same physician on pharmacy and medical claims. | Same MD Weight |
| 3. | Primary ICD-9 diagnosis code. | Primary Weight |
| 4. | ICD-9 diagnosis code on original file. | Original File Weight |
| 5. | Prescribing physician same specialty as physician submitting medical claim. | Same Specialty Weight |

*"After" means that pharmacy claim fill date is after date of service on medical claim. "Before" means that pharmacy claim fill date is before date of service on medical claim.

In the current embodiment, close proximity between the medical and pharmacy claim is considered the most important factor in assessing whether a drug has been prescribed for a particular disease, because it is assumed that much of the time the patient presents at a physician's office with a complaint, receives a prescription, and fills the prescription that day or soon thereafter. As shown in Table 11, the number of days between the medical claim and the pharmacy claim is broken into 9 categories. The time weight values A through I are constructed such that prescriptions given within 3 days of a face-to-face encounter are given maximum weight, and the time weight values drop off steeply after that point.

In the current embodiment, whether or not the prescribing physician is the same as the physician submitting the medical claim is the second most important factor in assessing the strength of a drug-to-diagnosis match. This addresses the scenario in which the physician sees the patient in his/her office, writes a prescription, then writes one or more appropriate diagnosis codes on the claim to be submitted for payment. In these situations, the prescription may be filled immediately, or if it is a prescription including refills, it can be filled several times. For drugs that treat chronic conditions, the fill date of the prescription can occur weeks or months after the date of the office visit. This criteria is weighted heavily so that links that are not close in time get a high link weight if the prescribing physician and the treating physician are the same, thus accounting for this situation where drugs are refilled repeatedly.

The third most important characteristic of a drug-to-diagnosis match is whether or not the ICD-9 code constituting the match is the primary diagnosis on the medical claim. It is assumed that diagnoses listed first on the claim constitute the main reason the patient was being seen by the physician and thus may represent the main reason for being prescribed a drug.

The fourth most important characteristic is whether the diagnosis code constituting the link is listed in the original drug-to-disease file. The original, "unexpanded" drug-to-disease file, as mentioned previously, was obtained from a national vendor of electronic pharmaceutical data. Although the disease indications added to the expanded drug-to-disease file are considered valid and reasonable, extra weight is given to the diseases listed in "unexpanded" drug-to-disease file because this file lists the most well-known labeled and non-labeled uses for drugs.

The least important characteristic in the weighting scheme of the present invention is whether the prescribing physician and physician submitting the medical claim are from the same specialty. This weight is included in order to capture instances where patients see many doctors from the same specialty clinic or group practice, any of whom are likely to write a prescription for the patient.

While this link weight scheme has been described in connection with the current embodiment of the invention, it will be understood that modifications to this scheme will be readily apparent to those skilled in the art. Future embodiments may contain different values for the various weighted characteristics, or the various categories within a characteristic might be altered (e.g., 5 categories instead of 9 for the time weight). Furthermore, future embodiments may contain a different list of characteristics for the link weight scheme. For example, a measure of the strength of association between the ICD-9 code and the drug might be added. In developing the drug-disease lookup table, physician consultants carefully scrutinized the list of diseases indicated for each drug and developed an exhaustive list of ICD-9 codes for each disease and, where necessary, added disease indications. It would be a straightforward exercise for physicians to rank the list of diseases for each drug in terms of clinical likelihood. If a drug had two indicated diseases, then, this clinical ranking scheme would indicate which of the two is the more clinically appropriate and/or frequently used reason for the drug. It is also a straightforward extension of the current logic to apply different link weight values to different types of drugs. The current embodiment uses one master lookup table to assign weight values; however, future embodiments may have a master lookup table for each type of drug—for example, for drugs that are used chronically versus those used on an acute, or as-needed basis.

After all links have been identified for a given pharmacy claim, the links are grouped based on ICD-9 diagnosis code. Recall that a link is formed when the diagnosis code on a medical claim matches a diagnosis code on the list of indicated diseases for the drug in question. Thus, links are formed based on one or more unique ICD-9 codes. The present embodiment of the invention identifies all such ICD-9 codes for each pharmacy claim and performs the following steps: (1) adds the link weight values together to produce an RX-ICD match strength value; (2) counts the number of links; and (3) determines the link with the highest link weight value among the links for a specific ICD-9 code. The algorithm for the RX-ICD match strength is set forth in Table 12 below.

TABLE 12

$$\text{RX-ICD}_x \text{ Match Strength} = \sum_{i=1}^{j} (\text{Link Weight}),$$

where x is a specific IDC-9 diagnosis code, and j is the number of links from a pharmacy claim to facility and provider claims with ICD-9 diagnosis code x.

The RX-ICD match strength is simply the sum of the individual link weight values for each ICD-9 code that linked to the pharmacy claim in question. The present invention adds the link weight values for each ICD-9 code that matched to a pharmacy claim in order to determine the order of strength of association between the drug and each ICD-9 code. Individual link weight values, in essence, give a measure of association between the drug claim and a particular occurrence of a diagnosis code—ie, a diagnosis code from a claim for a visit to a particular physician on a particular day. That diagnosis code may appear in a patient's medical claim history on another occasion, especially if the patient's condition requires frequent monitoring by a physician. When determining the order of strength of association between the drug being analyzed and each diagnosis code for which an association has been made, the present invention gives a higher weight to diagnosis codes that appear frequently in the patient's claim history. This is accomplished by summing the link weight value for the ICD-9 code for each time it appears in the patient's claim history and is linked to that pharmacy claim. Thus the RX-ICD match strength value incorporates frequency of diagnosis code into the determination of the order of association between the drug and diagnosis: generally speaking, the more times the ICD-9 code appears in a patient's medical claim history, the higher the RX-ICD match strength.

Besides creating the RX-ICD match strength for each ICD-9 code that linked to a drug claim, the present invention counts the number of links that comprise the RX-ICD match strength. It also determines the link with the highest value of link weight. The data generated is output to a file called the RX-ICD detail file. This file includes one observation per pharmacy claim-ICD-9 diagnosis code combination and includes at least the following data fields: Member ID number; Pharmacy claim audit number; ICD9 code that produced the match; RX-ICD match strength value; Number of links comprising the RX-ICD match strength value; and Unique facility or provider claim identification number of the link with the highest value of link weight. Pharmacy claims that do not have any drug-disease links will not be output to this file. The number of links comprising the RX-ICD match strength value is provided on this file so that the user can easily identify the number of links for each ICD9 code. The medical claim identification number of the claim with the highest value of link weight is provided on this file so that the user can go back to the claims data and perform further analysis on drugs and diseases using the medical claim with the "best" link to the drug.

In the present embodiment, information on up to six ICD-9 codes that linked to the pharmacy claim is output to the original claims data input file. The present invention ranks the RX-ICD match strength values in descending order and outputs the ICD-9 code of the top six matching codes to the original claims file. Pharmacy claims that had no drug-disease matches are untouched by the program. It is to be understood that using six as the number of matching codes merely indicates the number determined to be optimal in performing inventive processes disclosed in the present embodiment of the invention.

Figure 2:
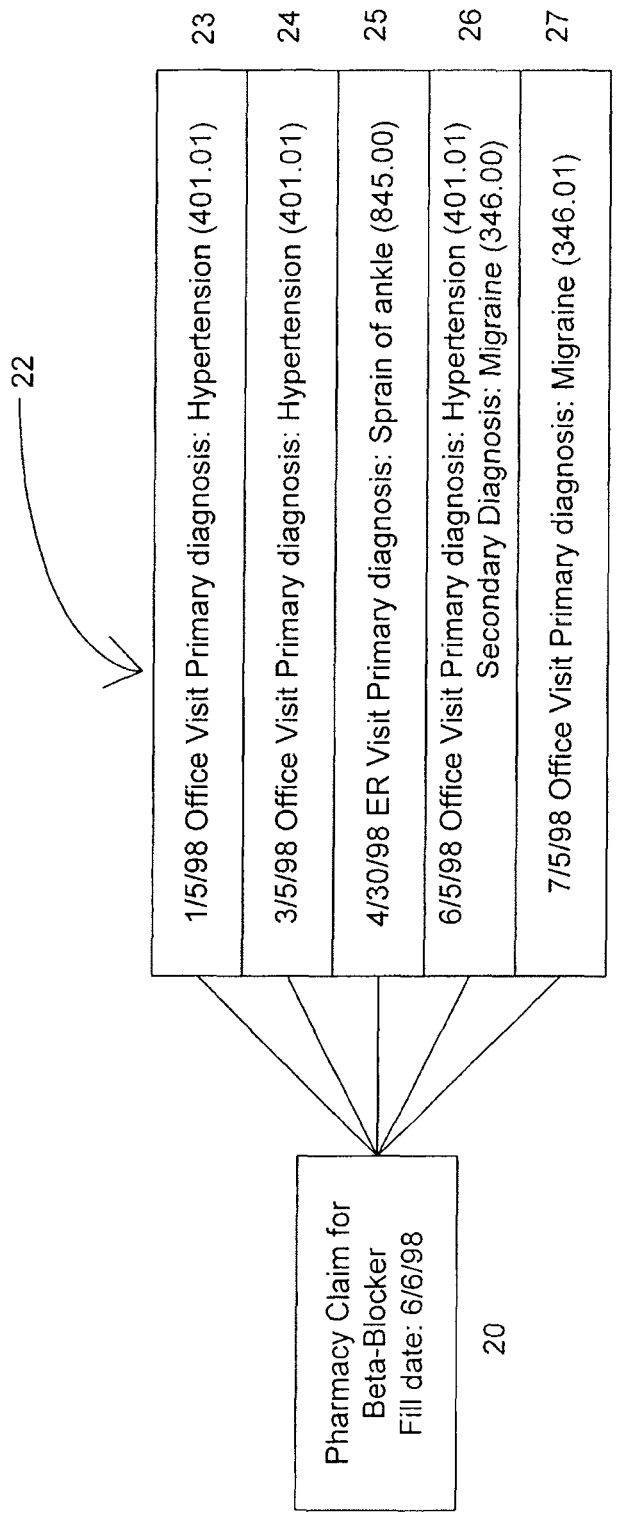
FIG. 2 illustrates an example of how links are created for a single pharmacy claim.

An illustration of how links for pharmacy claims are created are best shown by way of example. In this example, there is a single pharmacy claim for a 39-year old male patient filled on Jun. 6, 1998, for a 30-day supply of a beta-blocker, Atenolol. The NDC code on this pharmacy claim is 61392054330. Initially, the present invention looks up the NDC code for this claim in the NDC-DIN lookup table. NDC code 61392054330 maps to DIN 00245. Next, the Master Drug-to-Diagnosis Code table is accessed for DIN 00245 (refer to Table 8 for the CCG disease class indications for this drug). Referring to FIG. 2, the pharmacy claim 20 and the patient's assumed medical claims stream 22 are shown in their entirety. Within the medical claims stream 22, there are visits listing hypertension 23, 24, 26 sprain of ankle 25, and migraine 26, 27 as primary or secondary diagnoses. FIG. 2 also illustrates the links made with the medical claims data 22 for this single pharmacy claim 20. Hypertension 23, 24, 26 and migraine 26, 27 are both on the list of indicated diseases for Atenolol; sprain of ankle 30 is not. Accordingly, the sprain of ankle claim 25 is dropped from further consideration.

In the example medical claims data 22 illustrated in FIG. 2, there is illustrated two patient visits 26, 27 that list migraine as a diagnosis. However, the patient visits 26, 27 listing migraine as a diagnosis identify two different ICD-9 diagnosis codes. The office visit 26 lists 346.00, which refers to "Classical migraine, without mention of intractable migraine." The office visit 27 lists the diagnosis code 346.01, which is described as "Classical migraine, with intractable migraine, so stated." Thus for this pharmacy claim, three, not two, diagnosis codes have been matched.

Figure 3:
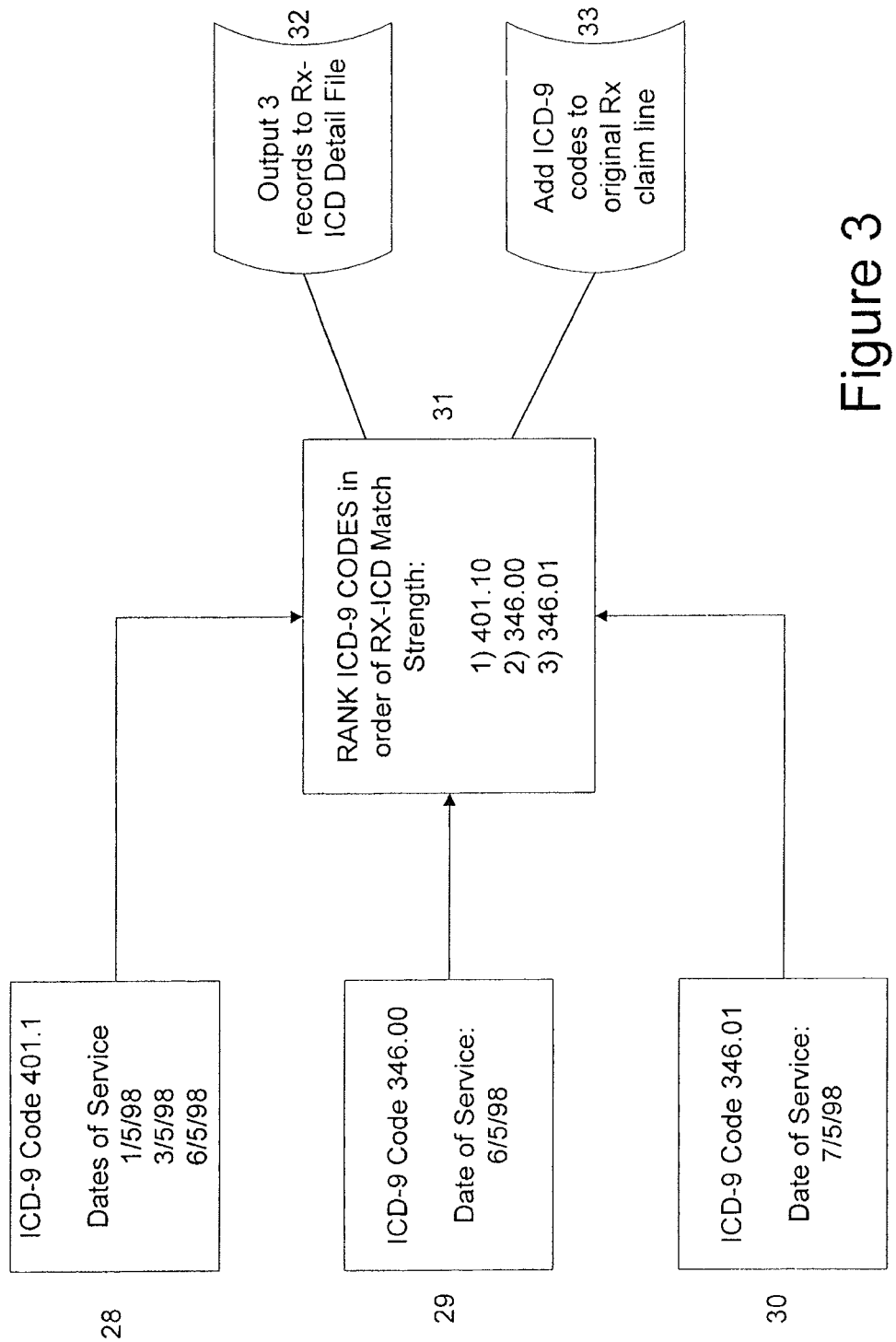
FIG. 3 illustrates the manner in which diagnosis codes for the pharmacy claim in FIG. 2 are ranked by link weight.

FIG. 3 illustrates the next step in the process, which is to add the link weight values for each ICD-9 code for the pharmacy claim illustrated in FIG. 2 and to rank the ICD-9 codes in order of RX-ICD match strength. The ICD-9 code 401.1, 28 ranks first, 346.00, 29 ranks second, and 346.01, 30 ranks last 31. Next, one record per ICD-9 code is output for this pharmacy claim to the RX-ICD detail file 32. It also adds these three ICD-9 codes to the original claims data record for the pharmacy claim, in ranked order 33.

System Modules

Figure 4:
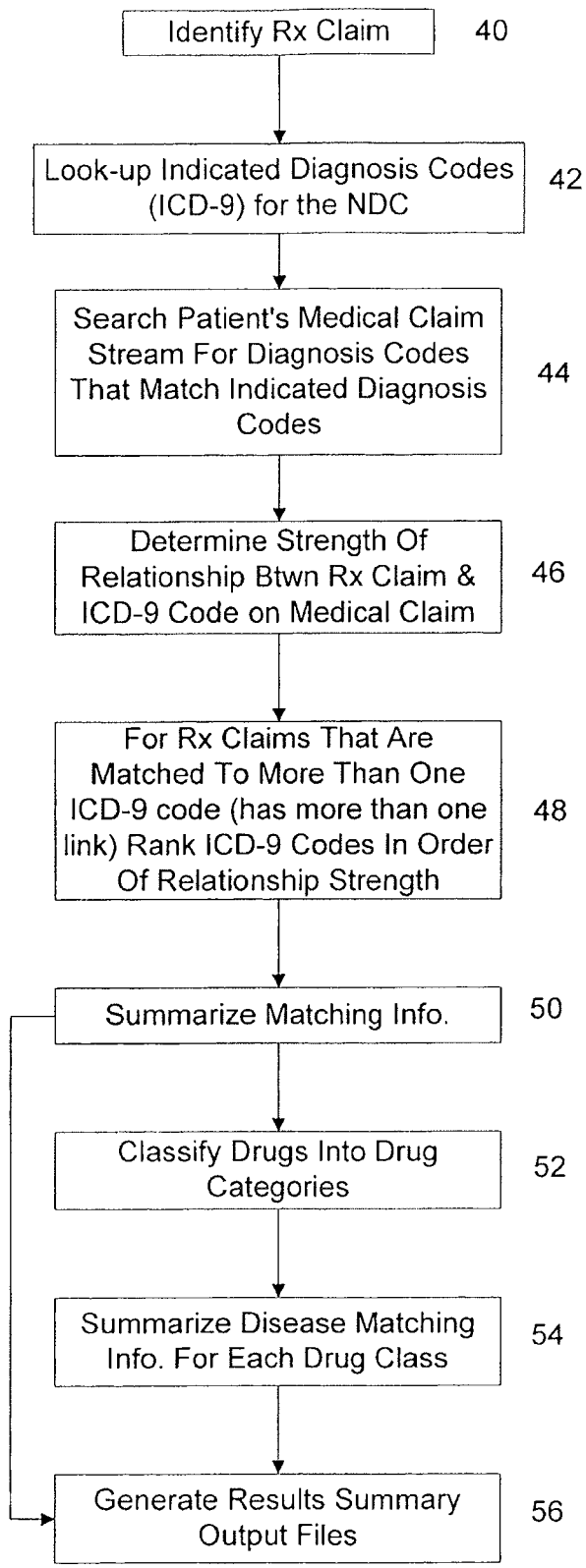
FIG. 4 is a flow diagram illustrating the general functional steps of the computer implemented method for matching drugs and diseases in accordance with the present invention.

The processing implemented by the present invention is performed by a Drug Disease Matching (DDM) module. The processing steps performed by the DDM module are illustrated FIGS. 4-8. Referred to FIG. 4, a summary of DDM module processing is illustrated. Following the identification of an individual patient's claim history to be analyzed, wherein the claims history includes pharmacy and medical claims data, a specific pharmacy claim for the individual patient is identified 40. Each pharmacy claim includes a National Drug Code (NDC). The drug indication number for the NDC code is extracted from a look-up table 41. The DDM module uses the DIN to determine the possible diseases associated with the drug identified in the pharmacy claim by way of a look-up table 42. The look-up table links the DIN to disease diagnosis codes (ICD-9 diagnosis codes) on medical (facility or provider) claims. Next, the patient's medical claim stream is searched for diagnosis codes that match the diagnosis codes 44 identified as being associated with the drug identified in the pharmacy claim. For all medical claims having the identified diagnosis code, DDM determines the strength of the relationship between each medical claim and the pharmacy claim 46. For each pharmacy claim that is matched to more than one diagnosis code, the diagnosis codes are ranked in order of relationship strength 48. Next, the matching information is summarized 50 and summary output files are generated 56. In an alternative embodiment, following summarization of the matching information 50, the drugs are classified into drug categories 52. Next, the disease matching information for each drug class is summarized 54, then summary output files are generated 56.

Figure 5A:
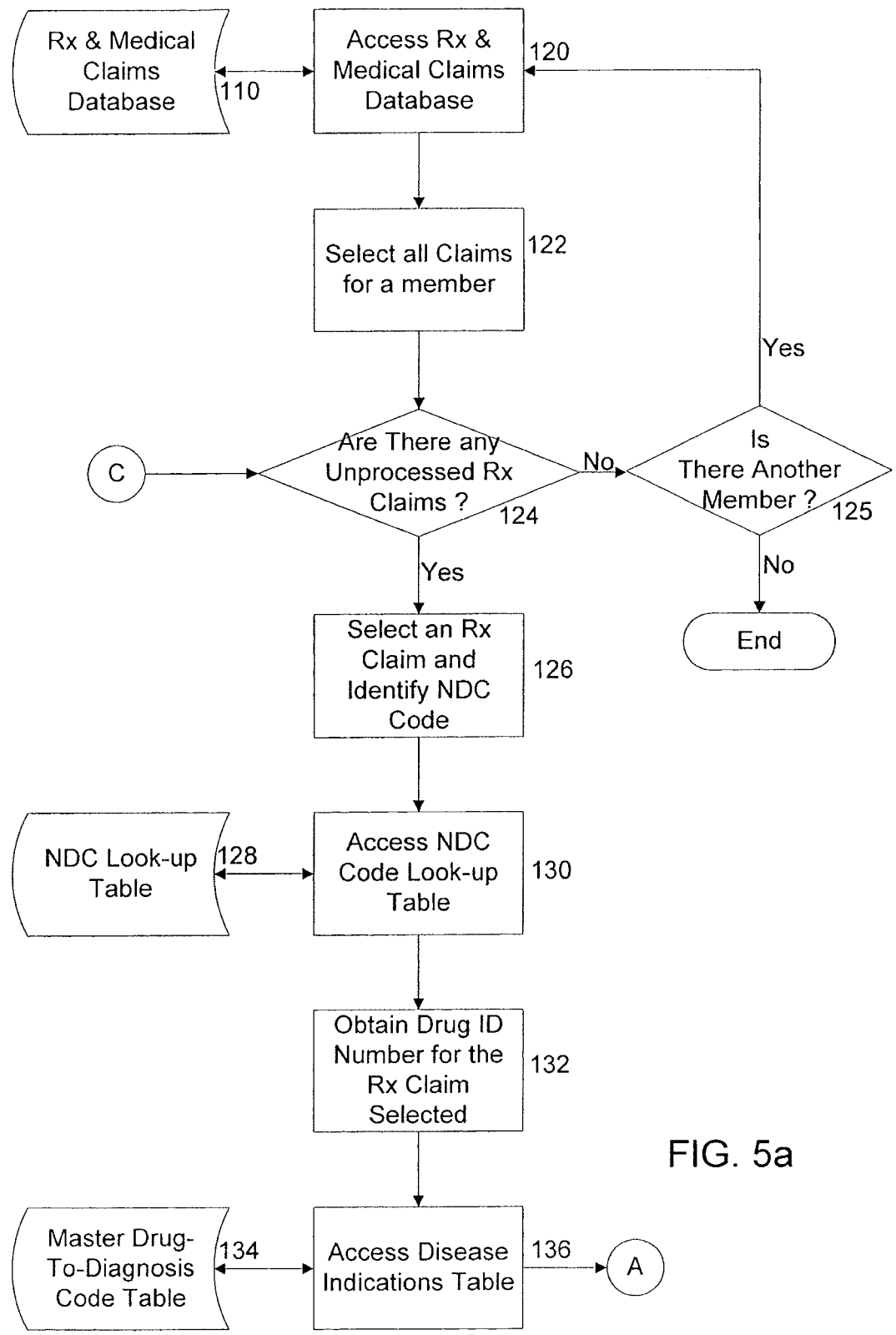
FIGS. 5a-5c illustrate a flow diagram for the general functional steps of an embodiment of the computer implemented method for matching drugs and diseases in accordance with the present invention.
Figure 5B:
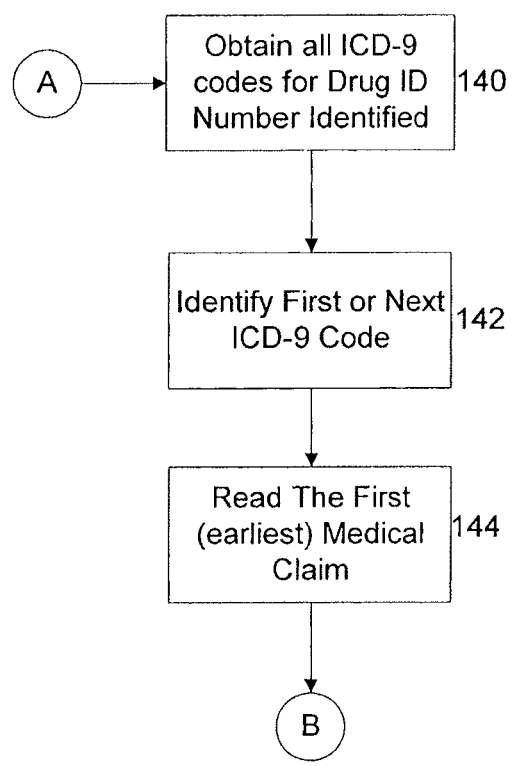
Figure 5C:
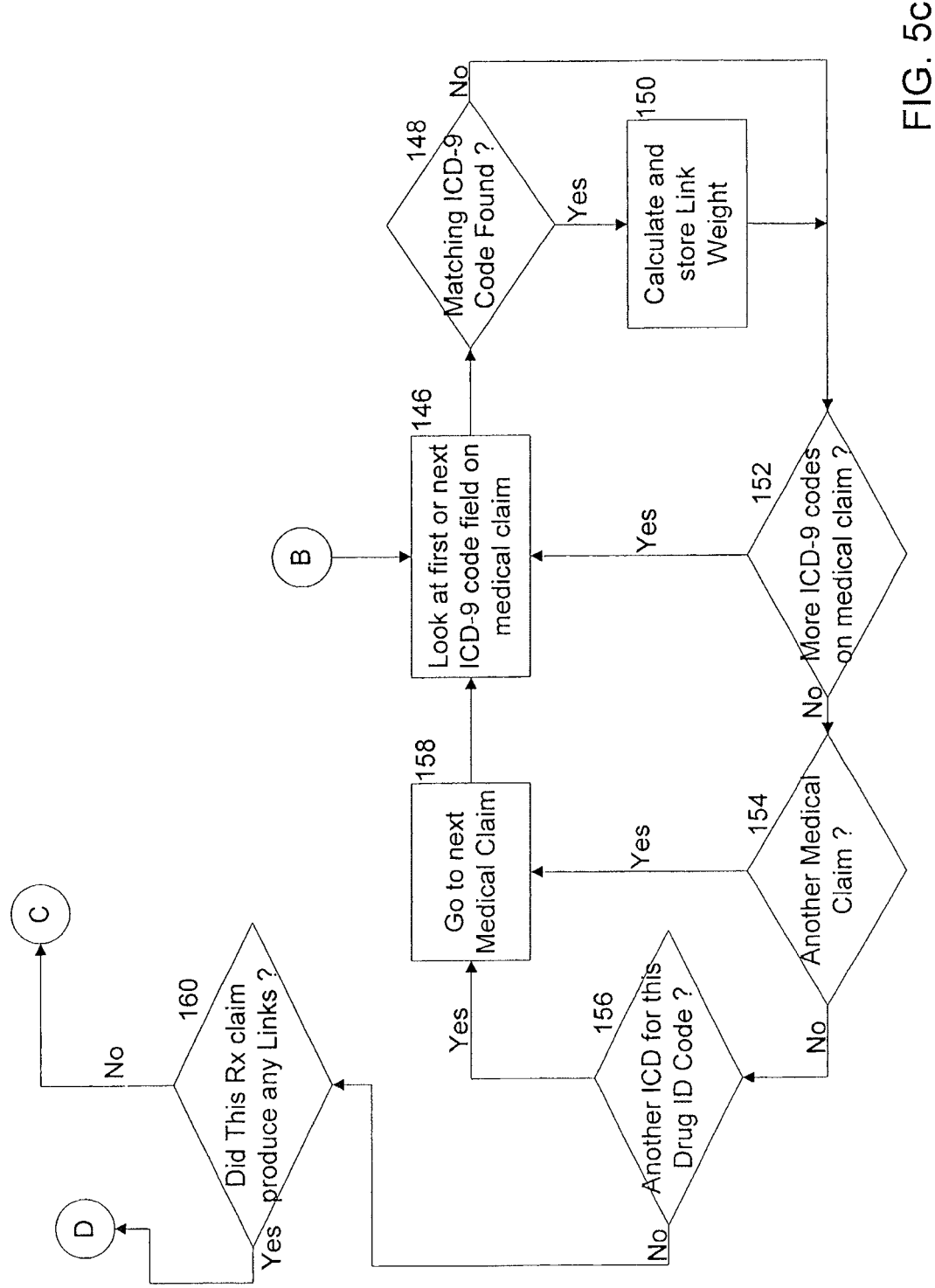

Referring to FIG. 5, the DDM module accesses the pharmacy and medical claims database 120 and selects all claims for a patient 122, including both pharmacy and medical claims. Next, it is determined whether there are any unprocessed pharmacy claims 124 for the patient identified. If all pharmacy claims have been processed, DDM determines whether there is another patient having pharmacy and medical claims data in the pharmacy and medical claims database that can be analyzed 125. If no patient exists, the DDM module concludes its analysis. If there are additional patients upon which the DDM module can perform an analysis upon their pharmacy medical claims, the process is initiated by selecting all claims for that particular patient 120, 122.

Following the selection of all pharmacy and medical claims for a patient, the DDM module determines whether there are unprocessed pharmacy claims 124 for the patient. If there are, a pharmacy claim is selected and its NDC code is identified 126. Next, the NDC look up table 128 is accessed 130 and the drug identification number for the pharmacy claim selected is obtained 132. Next the Master Drug-to-Diagnosis code table 134 is accessed 136 and all ICD-9 diagnosis codes associated with the drug identification number are identified and retrieved 140. The DDM module then identifies the first or next ICD-9 code for the ICD-9 codes obtained from the look-up table 142 and then begins to read the medical claims, reading the earliest medical claim first 144. In reading the first or earliest medical claim, the DDM module looks at the ICD-9 code field on the medical claim 146 to determine if there is a match between the ICD-9 code found in the medical claim and the ICD-9 code upon which the query is being performed. If there is a match between the ICD-9 code field of the medical claim being analyzed and the ICD-9 code upon which the query is being performed, the link weight for the matched ICD-9 code is calculated and stored 150. Next it is determined whether there are additional ICD-9 codes on the medical claim being analyzed 152. If there are, that ICD-9 code is compared to the ICD-9 code upon which the query is being performed to determine if there is a match 146. This process is performed until all ICD-9 codes on the medical claim being analyzed have been queried. If there are no additional ICD-9 codes on the medical claim 152 being analyzed, it is determined whether there are additional medical claims in the patient's medical claims history 154. If there are additional medical claims in the patient's medical claims history 158, a medical claim is selected and the first ICD-9 code field of the medical claim is queried 146. If there are no additional medical claims 154, it is determined whether there is another ICD-9 code for drug identification code 156 being analyzed. If there is another ICD-9 code for a drug identification number being analyzed, that ICD-9 code is queried against each medical claim in the patient's medical claims history 158 146. If there are no additional ICD-9 codes for that particular drug identification number 156, it is determined whether there are any links generated for the particular pharmacy claim 160 being analyzed. If there are no links generated for the pharmacy claim being analyzed, the DDM module determines whether there are any unprocessed pharmacy claims 124. If the pharmacy claim being analyzed did produce links, the DDM module performs the steps necessary to sort the links illustrated on FIG. 8.

Figure 6A:
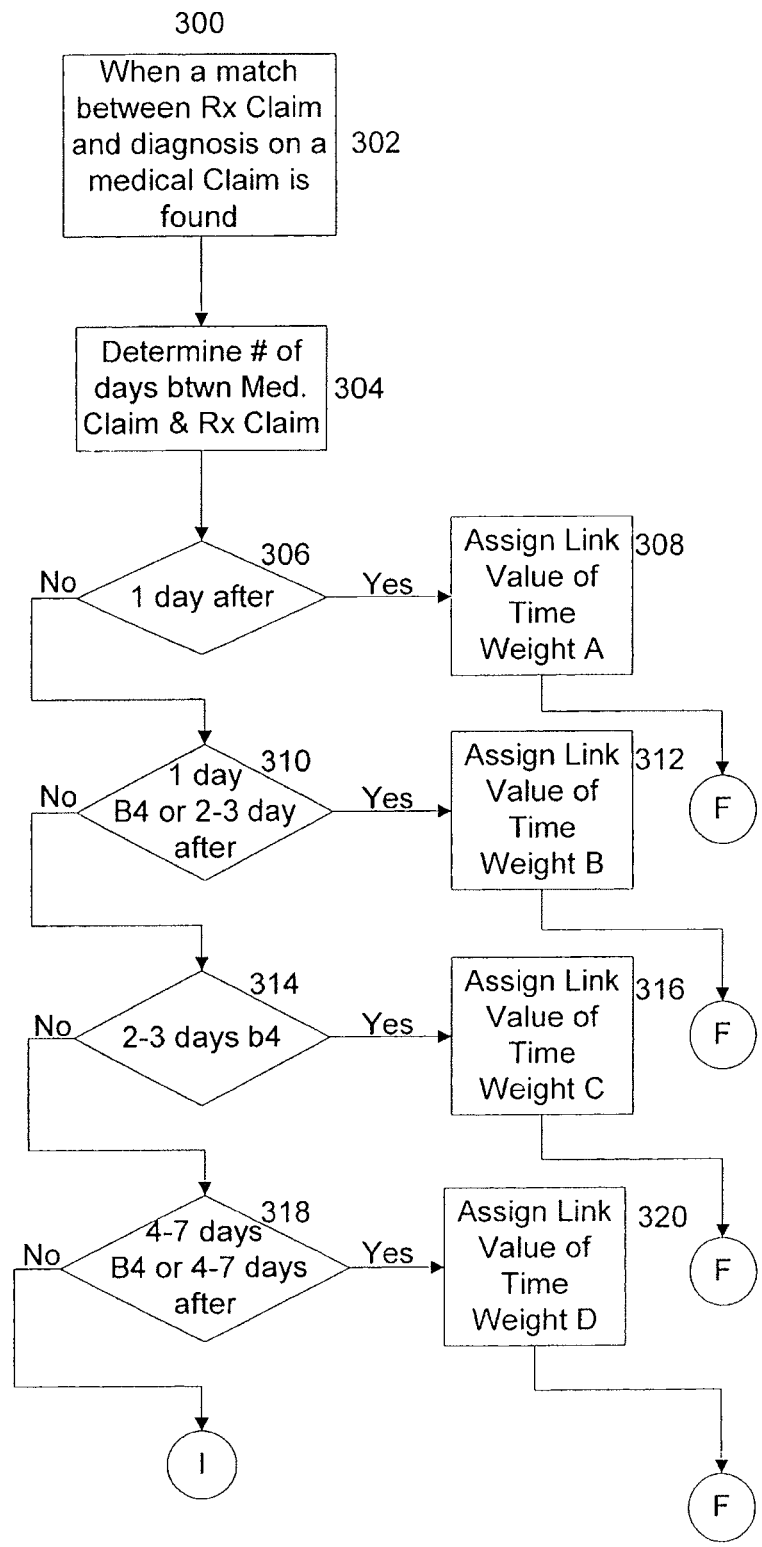
FIG. 6a-6b is a detailed flow diagram illustrating the functional steps of the link weight module used to assign a link weight between drugs that are matched to disease codes within a patient's medical history, in accordance with one embodiment of the present invention.
Figure 6B:
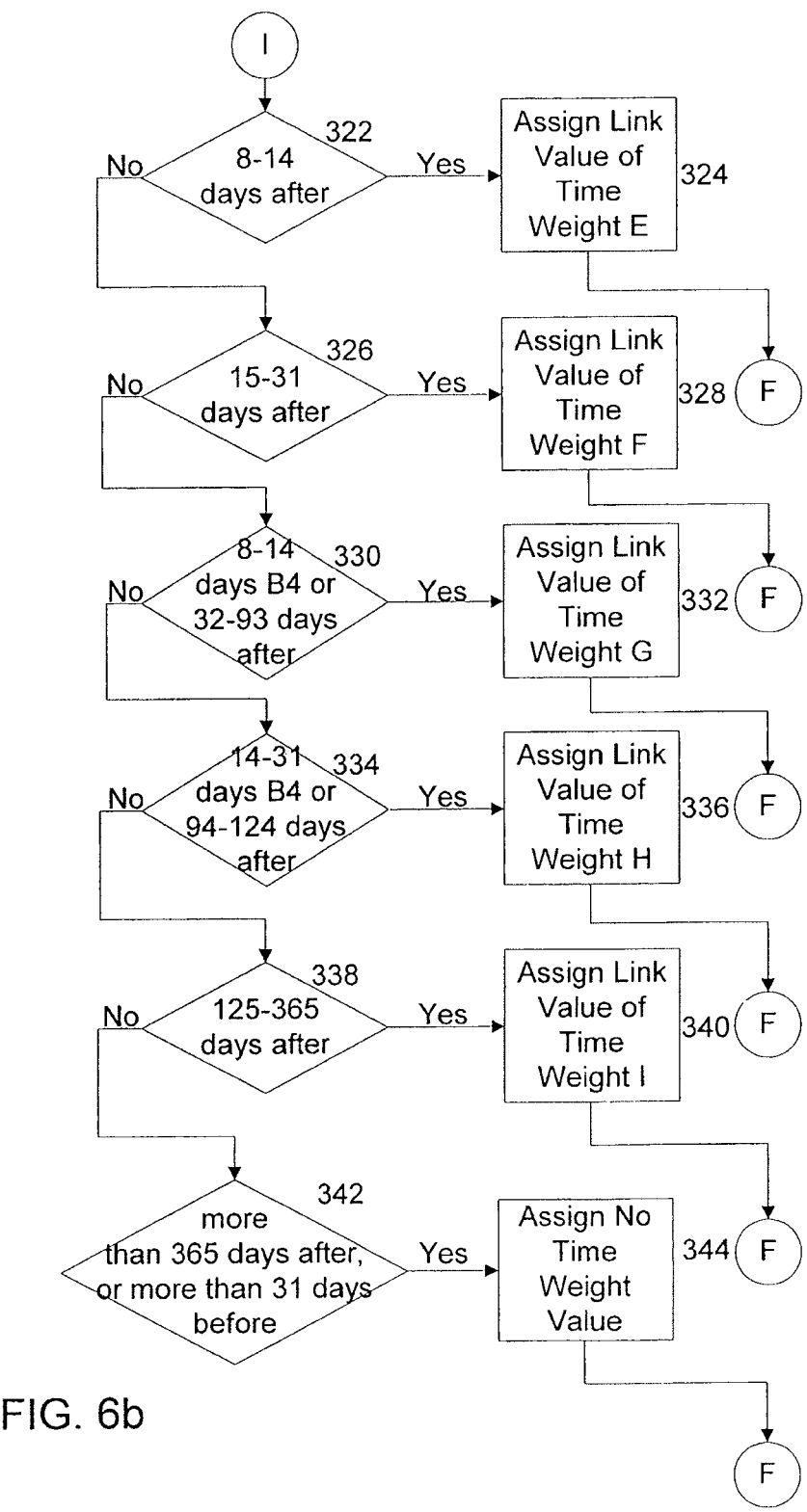
Figure 7A:
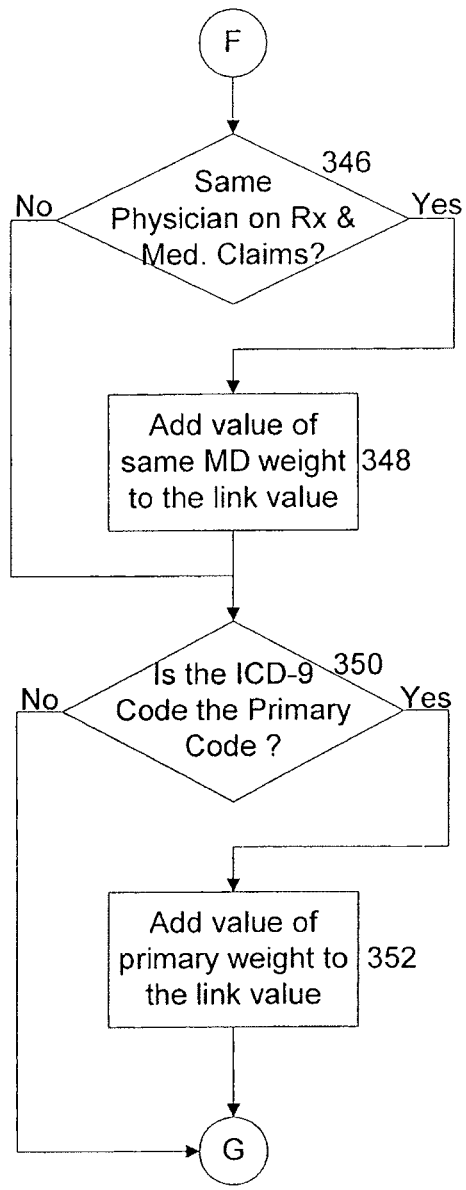
FIGS. 7a-7b is a detailed flow diagram illustrating further functional steps of the link weight module used to assign a link weight between drugs that are matched to disease codes within a patient's medical history, in accordance with one embodiment of the present invention.
Figure 7B:
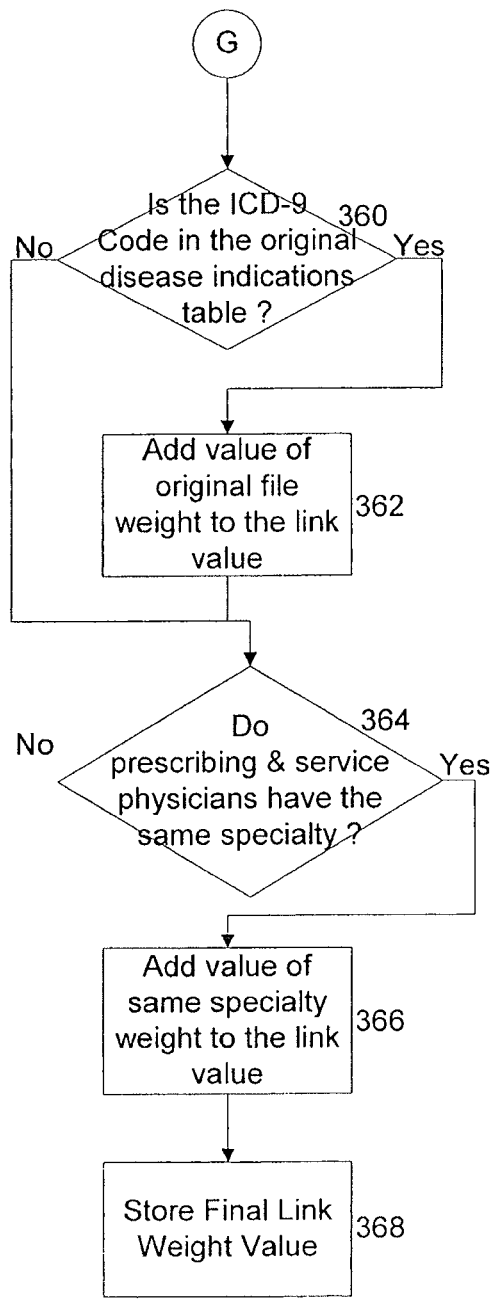

Referring to FIG. 6, when a match between a pharmacy claim and a medical claim is determined 302, the DDM module determines the number of days between the medical claim and the pharmacy claim 304. If the medical claim occurred on the same day or one day after the pharmacy claim 306, the value of time weight A is assigned to the match 308. If the medical claim did not occur on the same day or one day after the pharmacy claim 306, but occurred one day before or two to three days after the pharmacy claim 310, the value of time weight B is assigned to the match 312. If the pharmacy claim did not occur one day before or two to three days after the pharmacy claim 310, but did occur two to three days before the pharmacy claim 314, the value of time weight C is assigned to the match 316. If the pharmacy claim did not occur two to three days before the medical claim 314, but did occur four to seven days before or four to seven days after 318 the medical claim, the value of time weight D is assigned to the match 320. If the pharmacy claim did not occur four to seven days before or four to seven days after 318 the medical claim, but did occur eight to fourteen days after the medical claim 322, the value of time weight E is assigned to the match 324. If the pharmacy claim did not occur eight to fourteen days after the medical claim 322, but did occur fifteen to thirty one days after the medical claim 326, the value of time weight F is assigned to the match 328. If the pharmacy claim did not occur fifteen to thirty one days after the medical claim 326, but did occur eight to fourteen days before or thirty-two to ninety-three days after the medical claim 330, the value of time weight G is assigned to the match 332. If the pharmacy claim did not occur eight to fourteen days before or thirty-two to ninety-three days after the medical claim 330, but did occur fourteen to thirty-one days before or ninety-four to two hundred twenty-four days after the medical claim 334, the value of time weight H is assigned to the match 336. If the pharmacy claim did not occur fourteen to thirty-one days before or ninety-four to two hundred twenty-four days after the medical claim 334, but did occur one hundred twenty-five to three hundred sixty-five days after the medical claim 338, the value of time weight I is assigned to the match 340. If pharmacy claim did not occur one hundred twenty-five to three hundred sixty-five days after the medical claim 338, but did occur more than three hundred sixty-five days after or more than 31 days before the medical claim 342, no time weight value is assigned to the match 344. In the present embodiment, the values of time weights A-I are set in descending order. It is to be understood that the time weights A-I can be set at any value so long as they are in descending value order, with A having the greatest value and I having the least value.

After the link weight for the number of days between the pharmacy and medical claims has been established, the DDM module determines the second link weight characteristic, whether the prescribing physician is the same as the physician providing the service/office visit 346. Under circumstances where the prescribing physician is the same as the physician providing the service/office visit, the value of the same MD weight is added to the link value 348. If the prescribing physician is not the same as the physician providing the service/office visit, no additional value is added to the link value. The third link weight characteristic is whether the ICD-9 code is a primary or secondary diagnosis on the medical claim. When the disease selected during the process is the primary diagnosis on the medical claim 350, the value of the primary weight is added to the link value 352. The fourth link weight characteristic is to determine whether the ICD-9 code for the identified disease and medical claim is in the original disease indications table 360. If it is, the value of the original file weight is added to the link value 362. The fifth link weight characteristic is to determine whether the prescribing physician has the same specialty as the physician providing the service/office visit 364. Under circumstances where the prescribing physician and the physician providing the service/office visit have the same specialty, value of the same specialty weight is added to the link value 366. The DDM module finally stores the final link weight generated 368.

The values added to the link value when the prescribing physician and the physician providing the service/office visit are the same 348, value M, the value added to the link value when the disease selected during the process is the primary diagnosis 352, value N, the value added to the link value when the ICD-9 code for the identified disease in the medical claim is in the original disease indications table 362, value O and the value added to the link value when the prescribing and service physicians have the same specialty 366, value P, may all vary in future embodiments. In the present embodiment, values M, N, O and P have been set in greatest to least order, with value M being greatest, and value P being least. It is to be understood that values M, N, O and P do not have to be in any order. In one embodiment, the values for A-P are arranged such that the maximum value of link weight is 1.0. In this embodiment, a link weight of 1.0 refers to a "perfect match."

Figure 8A:
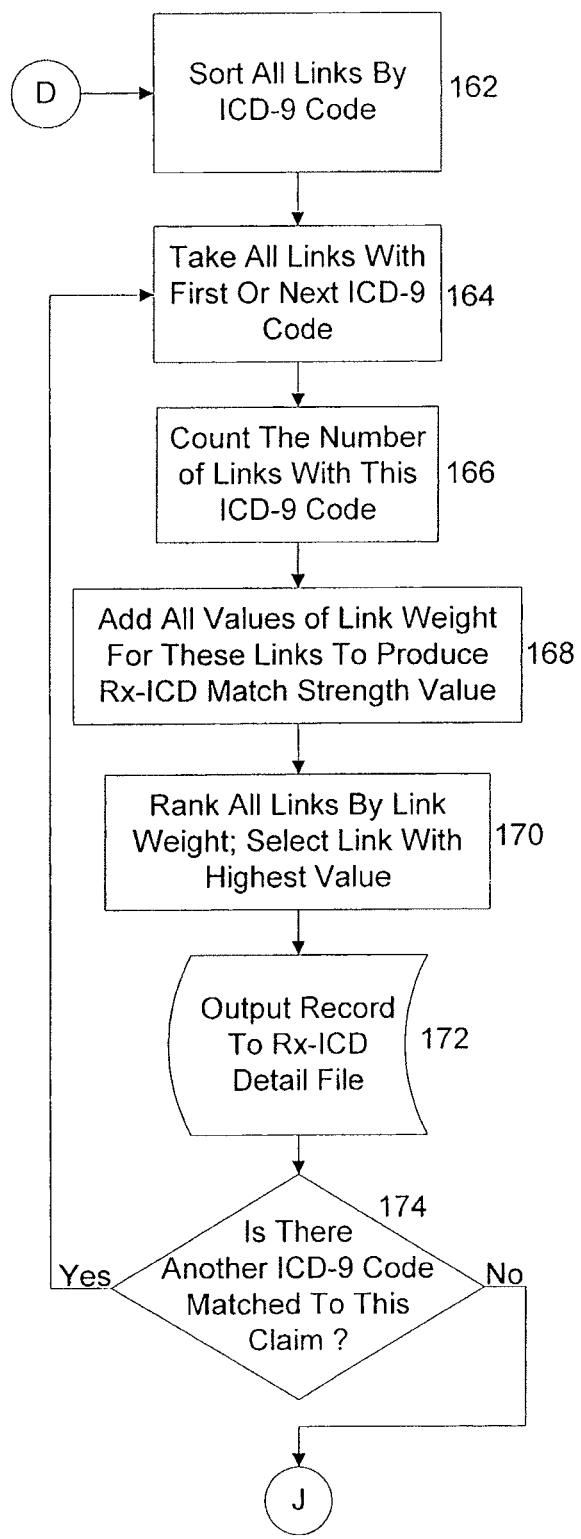
FIGS. 8a-8b illustrate a flow diagram for the general functional steps of an embodiment of the sort module within the computer implemented method for matching drugs and diseases in accordance with the present invention.
Figure 8B:
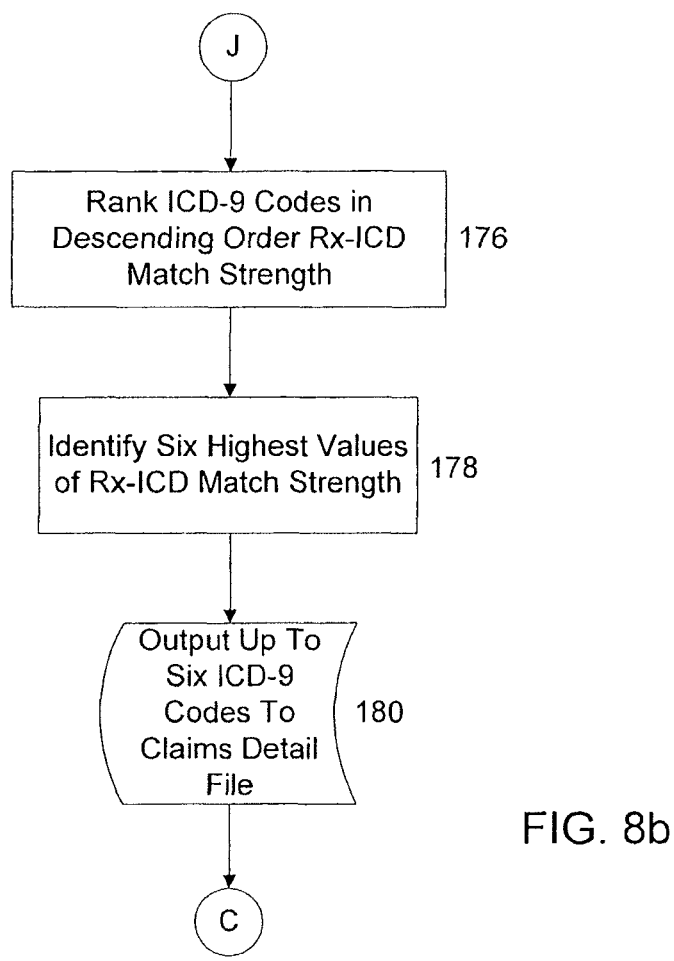

Referring to FIG. 8, is an illustration of the steps performed by the DDM module in sorting all links by ICD-9 code 162. The first step is to take all links with the first or next ICD-9 code 164. The next step is to count the number of links with a particular ICD-9 code 166. The next step is to add all values of link weight for these links to produce the RX-ICD-9 match strength value 168. The next step is to rank all links by link weight and select the link with the highest value 170. The DDM module then generates an output record to the RX-ICD detail file 172. It is then determined whether there is another ICD-9 code matched to this claim 174. If there is another ICD-9 code matched to this claim, steps 164 through 172 are performed on that ICD-9 code. If there are no other ICD-9 codes matched to this claim, the ICD-9 codes are ranked in descending order by RX-ICD-9 match strength 176. Next, the six highest RX-ICD-9 match strength values are identified 178 and output to the claims detail file 180.

While the present invention has been described in connection with the preferred embodiment thereof, it will be understood that many modifications will be readily apparent to those skilled in the art and this application is intended to cover any adaptations or variations thereof. It is manifestly intended that this invention be limited only by the claims and equivalents thereof.

What is claimed is:

1. A computer implemented system for establishing a relationship between drugs and diseases, the system comprising:
   a first memory area for storing a quantity of patient medical history billing records identifiable as patient prescription claim records and medical claim records,
   a second memory area storing a grouping of drug codes and a grouping of diagnosis codes,
   a processor coupled to said first memory area and said second memory area and configured to perform the following steps:
   (a) identify at least one prescription claim for a specific patient from said patient prescription claim records;
   (b) identify at least one drug identification code for said at least one prescription claim;
   (c) identify at least one disease associated with said at least one drug identification code;

(d) identify patient medical claims for said specific patient associated with said at least one disease, wherein each patient medical claim identified has at least one diagnosis code associated with said at least one disease; and (e) calculate a link weight value for each said at least one diagnosis code associated with said at least one disease, wherein said link weight value represents a degree of confidence that said at least one drug identification code for said at least one prescription claim is for a drug prescribed for said at least one disease identified that provides a statistical match association value to each said at least one diagnosis code within said patient medical claims identified as associated with said at least one disease.

2. The computer implemented system of claim 1 wherein said processor is further configured to perform the following step:

(f) generating a match strength value by adding each said link weight value calculated for each said at least one diagnosis code identified in said patient medical claims for said specific patient.

3. A computer implemented system for matching drugs and diseases, the system comprising:

a receiver for receiving a quantity of patient medical history billing records identifiable as patient prescription claim records and medical claim records, a data storage coupled to said receiver and configured to store a grouping of drug codes and a grouping of diagnosis codes, a processor coupled to said data storage arrangement and configured to perform the following steps:

(a) selecting a prescription claim of a specific patient from said patient prescription claim records and identifying at least one drug prescribed to said patient in accordance with said selected prescription claim;

(b) processing said at least one drug identified to determine at least one disease associated with said drug identified in said prescription claim; and (c) searching said medical claim records of said specific patient and identifying medical claims associated with said at least one disease; and (d) determining a link weight value, wherein said link weight value represents a degree of confidence that the at least one drug prescribed to said patient is for said at least one disease identified in the medical claims that provides a statistical match association value between said drug and each specific disease identified within said medical claims identified as associated with said at least one disease.

4. The computer implemented system of claim 3 wherein the step of identifying at least one drug prescribed to said patient in accordance with said selected prescription claim is implemented by identifying a national drug code in the pharmacy claim.

5. The computer implemented system of claim 3 wherein the step of searching said medical claim records of said specific patient and identifying medical claims associated with said diseases is implemented by performing the following steps:

(a) identifying at least one national drug code in the pharmacy claim;

(b) reading at least one predefined relationship between said at least one national drug code and at least one diagnosis code;

(c) reading said medical claim records of said specific patient and selecting medical claim records having said at least one diagnosis code.

6. The computer implemented system of claim 3 wherein the step of determining a link weight value is performed by the following steps:

(a) determining the number of days between said prescription claim selected and at least one of said medical claims identified as associated with said at least one disease; and (b) generating a link weight value based on said number of days in accordance with a preprogrammed formula.

7. The computer implemented system of claim 6 wherein said preprogrammed formula is a look-up table.

8. The computer implemented system of claim 3 wherein the step of determining a link weight value is performed by the following steps:

(a) determining whether a prescribing physician in the prescription claim is the same as a physician providing the service in the medical claim records; and (b) generating a link weight value in accordance with a preprogrammed formula when said prescribing physician is the same as said physician providing the service.

9. The computer implemented system of claim 3 wherein the step of determining a link weight value is performed by the following steps:

(a) determining whether a diagnosis code within said medical claims identified as associated with said at least one disease is a primary or secondary diagnosis within said medical claims; and (b) generating a link weight value in accordance with a preprogrammed formula when said diagnosis code within said medical claims identified as associated with said at least one disease is a primary diagnosis within said medical claims.

10. The computer implemented system of claim 3 wherein the step of determining a link weight value is performed by the following steps:

(a) determining whether a diagnosis code for said at least one disease and diagnosis codes within said medical claims identified as associated with said at least one disease are in an original disease indications table;

(b) generating a link weight value in accordance with a preprogrammed formula when said diagnosis code for said at least one disease and diagnosis codes within said medical claims identified as associated with said at least one disease are in an original disease indications table.

11. The computer implemented system of claim 3 wherein the step of determining a link weight value is performed by the following steps:

(a) determining whether a prescribing physician in the prescription claim has the same specialty as a physician providing the service in the medical claim records; and (b) generating a link weight value in accordance with a preprogrammed formula when said prescribing physician has the same specialty as said physician providing the service.

12. A computer implemented method of establishing a relationship between drugs and diseases comprising the following steps:

(a) storing a quantity of patient medical history billing records identifiable as patient prescription claim records and medical claim records in computer memory;

(b) storing a grouping of drug codes and a grouping of diagnosis codes in the computer memory;

(c) using a computer processor to identify at least one prescription claim for a specific patient from said patient prescription claim records;

(d) using the computer processor to identify at least one drug identification code for said at least one prescription claim;

(e) using the computer processor to identify at least one disease associated with said at least one drug identification code;

(f) using the computer processor to identify patient medical claims for said specific patient associated with said at least one disease identified, wherein each patient medical claim identified has at least one diagnosis code associated with said at least one disease identified; and (g) using the computer processor to calculate a link weight value for each said at least one diagnosis code associated with said at least one disease in accordance with a pre-programmed formula, wherein said link weight value represents a degree of confidence that said at least one drug identification code for said at least one prescription claim is for a drug prescribed for said at least one disease identified that provides a statistical match association value between said at least one disease identified and each said at least one diagnosis code within each said patient medical claim identified as associated with said at least one disease identified.

13. A non-transitory computer storage medium readable by a computing system and encoding a computer program of instructions for executing a computer process for establishing a relationship between drugs and diseases, said computer process comprising the steps of:

(a) storing in system data storage a quantity of patient medical history billing records identifiable as patient prescription claim records and medical claim records in memory;

(b) storing in system data storage a grouping of drug codes and a grouping of diagnosis codes;

(c) identifying at least one prescription claim for a specific patient from said patient prescription claim records;

(d) identifying at least one drug identification code for said at least one prescription claim;

(e) identifying at least one disease associated with said at least one drug identification code;

(f) identifying patient medical claims for said specific patient associated with said at least one disease identified, wherein each patient medical claim identified has at least one diagnosis code associated with said at least one disease identified; and (g) calculating a link weight value for each said at least one diagnosis code associated with said at least one disease in accordance with a preprogrammed formula, wherein said link weight value represents a degree of confidence that said at least one drug identification code for said at least one prescription claim is for a drug prescribed for said at least one disease identified that provides a statistical match association value between said at least one disease identified and each said at least one diagnosis code within each said patient medical claim identified as associated with said at least one disease identified.

* * * * *

UNITED STATES PATENT AND TRADEMARK OFFICE
CERTIFICATE OF CORRECTION

PATENT NO. : 8,645,171 B2
APPLICATION NO. : 13/612164
DATED : February 4, 2014
INVENTOR(S) : Gerald Lutgen et al.

Page 1 of 1

It is certified that error appears in the above-identified patent and that said Letters Patent is hereby corrected as shown below:

In the Specifications:

| Column | Line | PTO | Should Be |
|---|---|---|---|
| 9 | 45 | "CCG classes are 39×," [*multiplication symbol*] | —CCG classes are 39X,— [*letter*] |
| 9 | 46 | "Disorders" and 7800×," [*multiplication symbol*] | —Disorders" and 7800X,— [*letter*] |
| 14 | 9 [Table 12] | "where x is a specific IDC-9 diagnosis code," | —where x is a specific ICD-9 diagnosis code,— |

Signed and Sealed this
Sixth Day of May, 2014

Michelle K. Lee
*Deputy Director of the United States Patent and Trademark Office*